United States Patent [19]

Gerin et al.

[11] 4,140,761

[45] Feb. 20, 1979

[54] MODIFICATION OF HEPATITIS B VIRUS INFECTION IN CHRONIC CARRIERS OF HEPATITIS B SURFACE ANTIGEN

[75] Inventors: John L. Gerin; Hilton B. Levy, both of Bethesda, Md.; Thomas C. Merigan, Portola Valley, Calif.; Robert H. Purcell, Boyds, Md.; William S. Robinson, Palo Alto, Calif.

[73] Assignee: The United States of America as represented by the Department of Health, Education & Welfare, Washington, D.C.

[21] Appl. No.: 786,202

[22] Filed: Apr. 11, 1977

[51] Int. Cl.$^2$ .................. A61K 45/02; A61K 45/04; A61K 39/12; A61K 39/42
[52] U.S. Cl. ........................................ 424/85; 424/86
[58] Field of Search ................................. 424/85

[56] References Cited

PUBLICATIONS

Greenberg et al., Clinical Research 24:452A (1976).
Greenberg et al., New England J. of Medicine : 517–522, Sep. 2, 1976.
Purcell et al., The Lancet : 757–761, Oct. 9, 1976.
Desmyter et al., The Lancet : 645–647, Sep. 25, 1976.
Gerin Fractions No. 1, 1976.
Jacobs, Chem. & Eng. News : 24–27, Aug. 14, 1972.
Alter et al., New England J. Med. 295:909–919 (1976).
Okada, New England J. Med. 294:746–749 (1976).

*Primary Examiner*—Shep K. Rose
*Attorney, Agent, or Firm*—John S. Roberts, Jr.; Norman J. Latker; Thomas G. Ferris

[57] ABSTRACT

Interferon introduced parenterally in a human host or stimulated by an inducer (PICLC) for a period of greater than 21 days results in a major decrease in all markers of infectivity, such as DNA polymerase, and such markers remain at a depressed level during the period of treatment. Where PICLC is utilized to induce interferon in the host, a serum level of 50 units per milliliter or higher is necessary for effective clinical treatment and $17 \times 10^4 - 6.0 \times 10^3$ U/kg/day is an effective dose for exogenous interferon. Especially long-term treatment with exogenous interferon of greater than 21 days and up to 14 months results in clinical improvement for chronic hepatitis B virus (HBV) infection and this long-term treatment has resulted in sustained improvement even after cessation of treatment as well as resulting in a decrease in infectivity risk to others in close proximity to the infected human host. Such clinical improvement is marked by normalization of liver histology.

5 Claims, 5 Drawing Figures

MODIFICATION OF HEPATITIS B VIRUS INFECTION IN CHRONIC CARRIERS OF HEPATITIS B SURFACE ANTIGEN

The present invention relates to a method for treating chronic hepatitis B viral infections in humans as well as in chimpanzees and other primate species susceptible to the virus. The method comprises the injection of exogenous interferon or the induction of interferon by, for example, polyriboinosinic-polyribocytidylic acid-poly-1-lysine carboxymethyl cellulose complex (also known as Poly I Poly C complex or as PICLC), over an extended period of time to cause a reduction in the virus markers of hepatitis B infection. These markers are serum Dane particle-associated DNA polymerase, e antigen, hepatitis B surface antigen, intrahepatic hepatitis B surface and core antigens.

The decrease of the markers of infection by means of interferon or induced interferon is apparent within three weeks but the results are transient in that the markers return upon cessation of treatment. Longer treatment with exogenous interferon results in clinical improvement based on normal transaminase levels and further treatment (up to 14 months) results in apparent cure (normal liver histology) even on removal of treatment. A loss of markers means a decrease in infectivity risk to others in close contact and clinical improvement of patient means normalization of histology.

This invention relates generally to the use of interferon, either given exogenously or induced with PICLC, to modify viral infections and more specifically to the use of these substances as a method of modifying hepatitis B infections.

Interferon is a group of glycoproteins which induce resistance or result in host resistance to viral infections.

Recent epidemiological studies indicate as many as 150,000,000 to 200,000,000 people in the world are chronically infected with hepatitis B virus (HBV) at any one time. Most chronic HBV infections persist for many years and can transmit infection by blood transfusion and by nontransfusion-associated routes. Due to the large number of chronic carriers worldwide and the common occurrence of neonatal transmission from mothers who are chronic carriers, elimination of this virus by vaccination is unlikely in the foreseeable future. Therefore, another method is necessary and this invention treats chronic hepatitis viral infection in a manner which actually modifies the virus infection by decreasing the virus markers and is a treatment which, if continued for an extended period of time, will substantially minimize the risk of a relapse in the human host to a state of chronic illness marked by increased infectious markers. This result can be accomplished by a prolonged injection schedule with either exogenous interferon or an interferon inducer such as PICLC.

TYPE B HEPATITIS

Figure 1A:
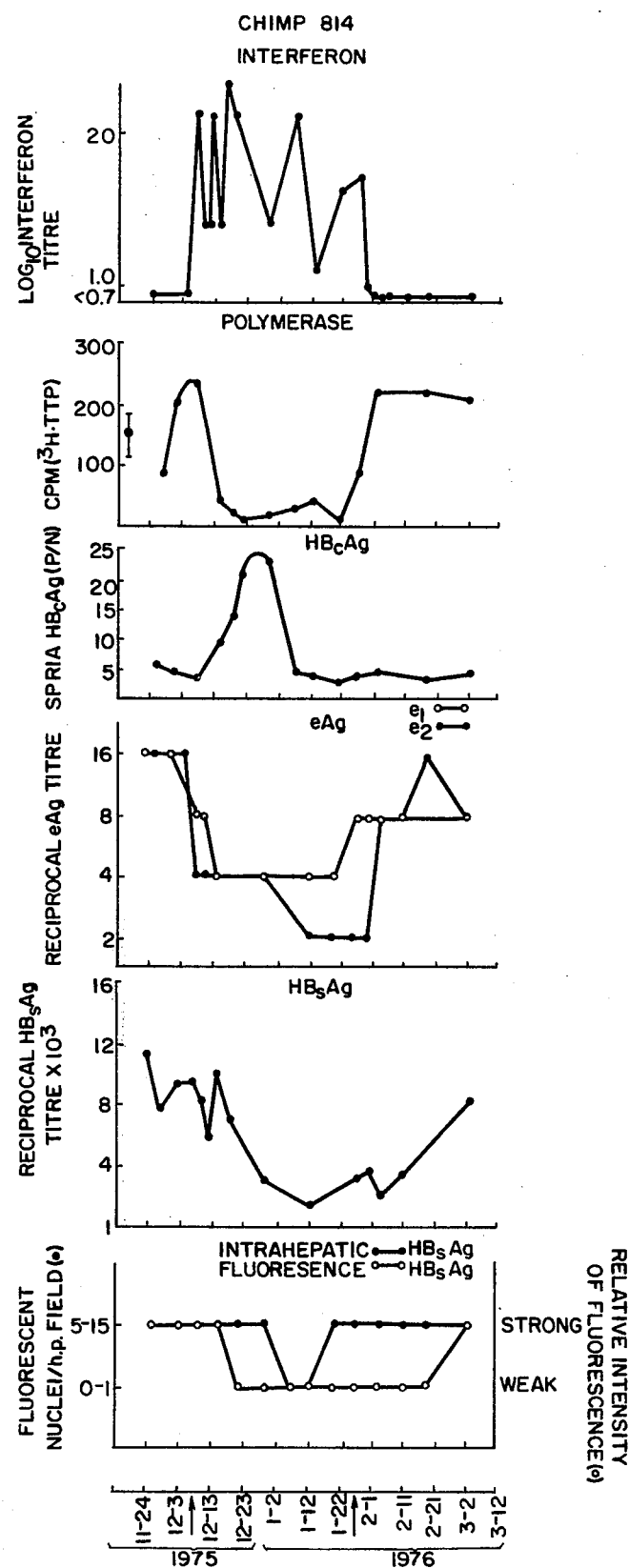
FIGS. 1a and 1b illustrate the effect of treatment with PICLC on markers of chronic hepatitis B virus infection in chimpanzees (814) and (821), the beginning and end of the treatment periods are indicated by arrows on the abscissa.

Type B hepatitis represents a serious public health problem. In the United States, it is estimated that approximately 150,000 cases of Type B occur per year (based on 1973 statistics). An increasing proportion of these cases in recent years are associated with the use of drugs in the 15 to 29 year age group. Other groups at high risk of infection include recipients of blood and blood products, instiutionalized patients, the staff and patients of hemodialysis units, medical laboratory workers, and military personnel. Interestingly, only a small proportion of infected individuals develop overt disease. The more common response is a subclinical infection. In fact, a serious concern is the development of the chronic carrier state in a proportion of infected individuals. Besides parenteral transmission, contact transmission and vertical transmission from mother to offspring now appear to be well established routes of infection. Therefore, the chronic carrier is not only at risk to progressive liver disease, but also represents a potential reservoir of infection to susceptible contacts.

In 1963 Blumberg et al, investigating ethnic markers among Australian aborigines, discovered a low-density serum lipoprotein which turned out to be a unique antigen which was termed the Australia antigen (Au). Au is now known as the hepatitis B surface antigen ($HB_sAg$) which is the specific antigen for type B hepatitis. It is also known that the hepatitis B surface antigen is associated with several distinct particulate structures. The predominant form is a spherical particle with an average diameter of 22 nm; also found are filaments 22 nm in diameter and varying in length, and a 43-nm spherical particle with a complex morphology.

THE VIRUS

There now exists a considerable amount of evidence indicating that the 43-nm particle represents the virus of Type B hepatitis. Dane et al [Lancet 1:695 (1970)] first described its association with $HB_sAg$ and this particulate form is commonly referred to as the "Dane" particle. The Dane particle has a complex morphology with an external lipoprotein coat ($HB_sAg$) and an internal 27-nm core. Almeida et al [Lancet 2:1225 (1971)] demonstrated that the core represents a distinct antigen, quite separate from $HB_sAg$, and now referred to as hepatitis B core antigen or $HB_cAg$. The core may be released by disruption of the Dane particle with non-ionic detergents or ether and purified from the coat by density gradient centrifugation. Essentially all chronic $HB_sAg$ carriers circulate antibody to the core of the Dane particle.

The evidence that the Dane particle is the virus of Type B hepatitis is largely circumstantial but convincing. The Dane particle expresses virus-specific determinants ($HB_sAg$) on its outer surface and antibodies to these determinants protect against infection with live virus. The Dane particle contains an endogenous DNA polymerase within its core and the appearance of polymerase-containing Dane particles during the acute phase of HBV infection resembles the viremias of other virus infections.

Recent studies have shown that DNA polymerase is a direct risk factor in horizontal transmission of disease (cf. Alter et al, *New England Journal of Medicine*, 295:909-919, 1976). It has been further noted in the literature that there is also a direct correlation between DNA polymerase and the e antigen as risk factors in vertical transmission (i.e., mother to offspring) (cf. Okada, *New England Journal of Medicine*, 294:746-749, 1976).

THE DOSAGE

The therapeutic dosage of exogenous interferon is $17 \times 10^4$ - $6.0 \times 10^3$ U/kg/day for greater than 21 days to remove markers such as DNA polymerase and up to 14 months to remove $HB_sAg$ to acceptable therapeutic levels and remove the disease transmitting capability of the patient as a carrier. As a convenience, the appropriate dosage may be administered on alternate days.

Parenteral PICLC as an inducer is utilized in equivalent amounts so that in both cases the effect of the inducement is to produce a serum blood level in the host of at least 50 U/ml or higher. A biologic standard unit (U) for interferon is a unit of viral inhibition previously set out and utilized in the Levy U.S. Pat. No. 3,952,097.

PRIOR ART

Patents

U.S. Pat. No. 3,692,899 Levy relates to a process affecting the growth of transplanted malignant tumors in mice by an effective dose of polyinosinic-polycytidylic acid.

U.S. Pat. No. 3,952,097 Levy shows poly ICLC useful as an injectable in levels associated with antiviral effects such as "protecting rhesus monkeys against Simian hemorrhagic fever virus as well as yellow fever virus."

Literature

Jacobs, "Hepatitis Research Nears Breakthrough," *Chem. & Eng. News*, Aug. 14, 1972, pages 24-27.

Gerin, "Hepatitis, the Search for Viral and Sub-Viral Antigens," Fractions, No. 1, 1976.

Desmyter et al, "Administration of Human Fibroblast Interferon in Chronic Hepatitis-B Infection," *The Lancet*, Sept. 25, 1976, pages 645-647.

Purcell et al, "Modification of Chronic Hepatitis-B Virus Infection in Chimpanzees by Administration of an Interferon Inducer," *The Lancet*, Oct. 9, 1976, pages 757-761.

Greenberg et al, "Effect of Human Leukocyte Interferon on Hepatitis B Virus Infection in Patients With Chronic Active Hepatitis," *The New England Journal of Medicine*, Sept. 2, 1976, pages 517-522.

Greenberg et al, "The Effect of Human Interferon on Hepatitis B Virus Associated DNA Polymerase in Chronically Infected Individuals," *Clinical Research*, 24:452A (1976).

It can be shown in the following examples that a sustained dosage preferably a sustained equivalent daily dosage of $17 \times 10^4$ - $6.0 \times 10^3$ U/kg of exogenous interferon or induced interferon maintained at a level of 50 U/ml or higher, as with PICLC, leads to a reduction in the markers associated with hepatitis B. In the case of dosage by exogenous interferon administered for a time period exceeding 21 days and up to 14 months, these infections markers such as DNA polymerase are reduced in concentration to undetectable values and do not return.

EXAMPLE 1

Short-Term Therapy (Two Weeks) — Chimpanzees

The $HB_sAg$-positive chimpanzees No. 814 and 821 were administered 3 mg/kg PICLC once daily for seven consecutive days and every other day for an additional week. Dosage amounts and rates were based on previous and current experience and the data shown in Table 1 in which a single 3 mg/kg dose stimulated good levels of interferon in both a normal and chronic carrier chimpanzee. Baseline values were determined during the two weeks preceding and succeeding the treatment period. Plasma samples were obtained 24 hours after each infusion of PICLC and daily to weekly during the pre- and post-treatment periods.

The administration of PICLC had a profound effect on chronic HBV infection in chimps 814 and 821 (see Table 2). The response was more marked in chimp 821 in which interferon activity was still detectable 24 hours after administration throughout almost the entire treatment period. In contrast, interferon was detected only 6 consecutive days of the treatment period in chimp 814. Changes in indicators of HBV infection paralleled the interferon response in the chimpanzees. DNAP (hepatitis B-specific DNA polymerase) activity fell to undetectable levels within two days of initiation of treatment in chimp 821 and remained undetectable until cessation

TABLE 1

Serum Interferon Levels Following a Single Intravaneous Infusion of PICLC (3 mgm/Kg) in Chimpanzees

| Interval (hrs.) After Infusion | Interferon Titer in Indicated Chimp (units/ml) | |
|---|---|---|
| | #14 (normal) | #800 ($HB_sAG$ Carrier) |
| Pre | <10 | <10 |
| 2 | <10 | 40 |
| 4 | <10 | 40 |
| 8 | 20 | 160 |
| 12 | 160 | 20 |
| 24 | <10 | <10 |
| 36 | <10 | <10 |
| 48 | <10 | <10 |

TABLE 2

Effect of 14-Day Treatment with PICLC on Indicators of Chronic Hepatitis B Virus Infection in Chimpanzees

| Indicator | Response in Indicated Chimp | |
|---|---|---|
| | #814 | #821 |
| Serum | | |
| DNA polymerase | Diminished | Markedly diminished |
| e antigen | Slightly diminished | Markedly diminished |
| $HB_sAg$ | Unchanged | Unchanged |
| Alanine amino transferase | Slightly elevated | Slightly elevated |
| Liver | | |
| $HB_sAg$ | Unchanged | Unchanged |
| $HB_cAg$ | Unchanged | Unchanged | of treatment, at which time it returned to pretreatment levels. DNAP in the serum of chimp 814 also rapidly fell to undetectable levels but returned to pretreatment levels a week before treatment was terminated. The titer of e antigen fell only two-fold in this latter animal but fell four- to eight-fold in chimp 821. The titers of $HB_sAg$, anti-$HB_s$, and anti-$HB_c$ in the serum and the quantity of $HB_sAg$ and $HB_cAg$ in the liver remained essentially unchanged in both animals during the experiment, as did the histologic findings. Alanine aminotransferase activity became slightly elevated during PICLC treatment in both animals. All laboratory values that were altered by PICLC returned to pretreatment levels following cessation of treatment.

After it had been determined that increasing interferon levels in chimpanzees with chronic hepatitis was not unduly hazardous, parallel studies on the long-term effects of exogenous interferon on humans and of PICLC on chimpanzees were initiated and are described in Examples 2 and 3.

EXAMPLE 2

Long-Term Therapy (7 Weeks) — Chimpanzees

Chronic carrier chimpanzees 814 and 821 and normal control chimpanzees 16 and 105 were employed in the study of the effects of prolonged PICLC administration on chronic HBV infection and on normal physiology. After two weeks of baseline studies, chimpanzees 814, 821, and 105 were administered 3 mg/kg body weight PICLC, and chimpanzee 16 was administered the carboxymethyl cellulose (CMC) used to stabilize the PICLC complex. PICLC was administered once daily for two six-day periods, separated by one non-treatment day, and every other day thereafter for a total of seven weeks. Serum samples were drawn 8 hours after administration of PICLC or CMC for measurement of interferon levels, and plasma samples were obtained immediately prior to PICLC administration at daily to weekly intervals. Biopsies were obtained weekly.

Chimp 814 developed moderate levels of serum interferon within eight hours of administration of PICLC and maintained a responsiveness to PICLC throughout the study (FIG. 1a). Within a week after the initiation of PICLC treatment, serum DNAP fell to baseline levels and remained there throughout the treatment but returned to pre-treatment levels within a week of cessation of PICLC infusion. Coincident with the fall of DNAP activity, serum $HB_cAg$ increased markedly, reaching a peak almost six times greater than baseline values at the time that DNAP levels reached their lowest point.

A pool of plasma concentrates from the period of peak $HB_cAg$ activity was banded in a cesium chloride gradient. After treatment of the fractions with detergent, $HB_cAg$ was detected in those fractions which corresponded to the density region of Dane particles (1.21–1.23 g/cm$^3$) and not in the region of free core particles (>1.28 g/cm$^3$). Therefore, the $HB_cAg$ appeared to be associated with Dane particles deficient in DNAP activity. Thus, the administration of PICLC and the resultant induction of endogenous interferon caused the synthesis and/or release of presumably defective hepatitis B virions. As can be seen in FIG. 1a, the titer of both the $e_1$ and $e_2$ components of e antigen paralleled the course of DNAP activity during the treatment period. Within three weeks of initiation of PICLC therapy, serum $HB_sAg$ began to decline in titer and subsequently fell to levels only approximately one-fourth of the pretreatment level.

Following cessation of treatment, serum $HB_sAg$ returned to pre-treatment levels. Intrahepatic $HB_cAg$ transiently fell to barely detectable levels midway through the treatment period but had returned to pretreatment levels before cessation of treatment. The effect of PICLC treatment on intrahepatic $HB_sAg$ was more marked: $HB_sAg$ fell to barely detectable levels in the liver in parallel with the fall in serum $HB_sAg$ titer and remained barely detectable until serum $HB_sAg$ increased in titer following discontinuance of treatment. It was of interest that the decline in intrahepatic $HB_cAg$ was characterized by a decrease in the number of fluorescing nuclei without a concomitant decrease in the intensity of fluorescence in individual nuclei, whereas loss of intrahepatic $HB_sAg$ was characterized by a marked decrease in the intensity of cytoplasmic fluorescence of almost all effected cells. The mild type B hepatitis observed during the first experiment had resolved by the time the second experiment began; only non-specific histologic changes were observed during this second infusion of PICLC.

Figure 1B:
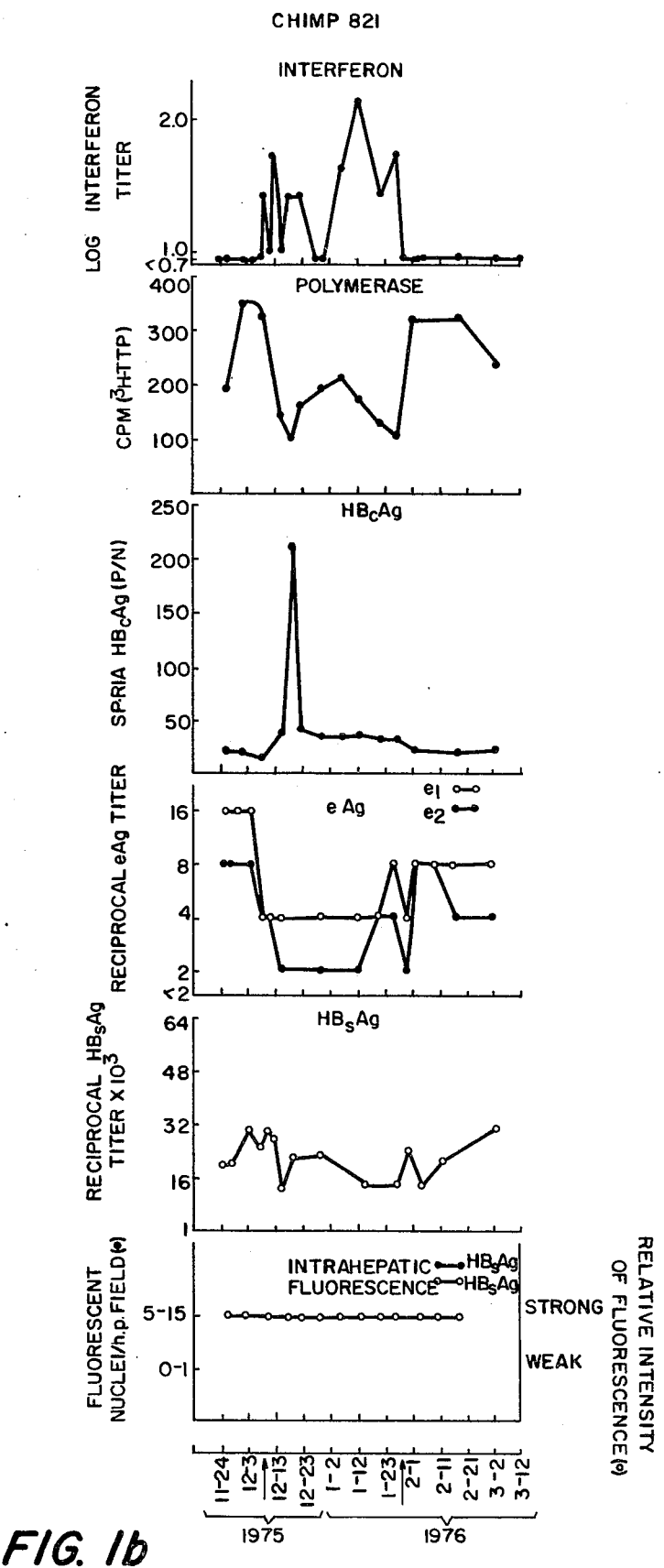

Similar results were obtained with chimp 821 (FIG. 1b). The induction of endogenous interferon was less marked in this animal: serum interferon titers averaged one-third those of chimp 814. Nevertheless, serum DNAP fell to low levels and remained there throughout the treatment period, indicating a striking sensitivity of the hepatitis B virus to low levels of interferon.

The interferon response of chimpanzee 105 was essentially identical with that of chimp 814; interferon was not detected in any of the serum specimens from chimp 16, who received only CMC. Histologic findings in chimp 16 were unremarkable, but chimp 105 developed a reactive hepatitis characterized by activation of Kupffer cells and deposition of fat in hepatocytes. These changes were suggestive of hepatoxicity.

EXAMPLE 3

Humans

The human subjects for the third example were chosen from 25 $HB_sAg$ positive patients with biopsy documented chronic active hepatitis (CAH). Three subjects (Patient 1, age 21; Patient 2, age 32; Patient 3, age 30 years) had elevated levels of serum particle-associated DNA polymerase. In addition, one subject (Patient 4, age 40) without detectable DNA polymerase was given interferon.

Figure 2:
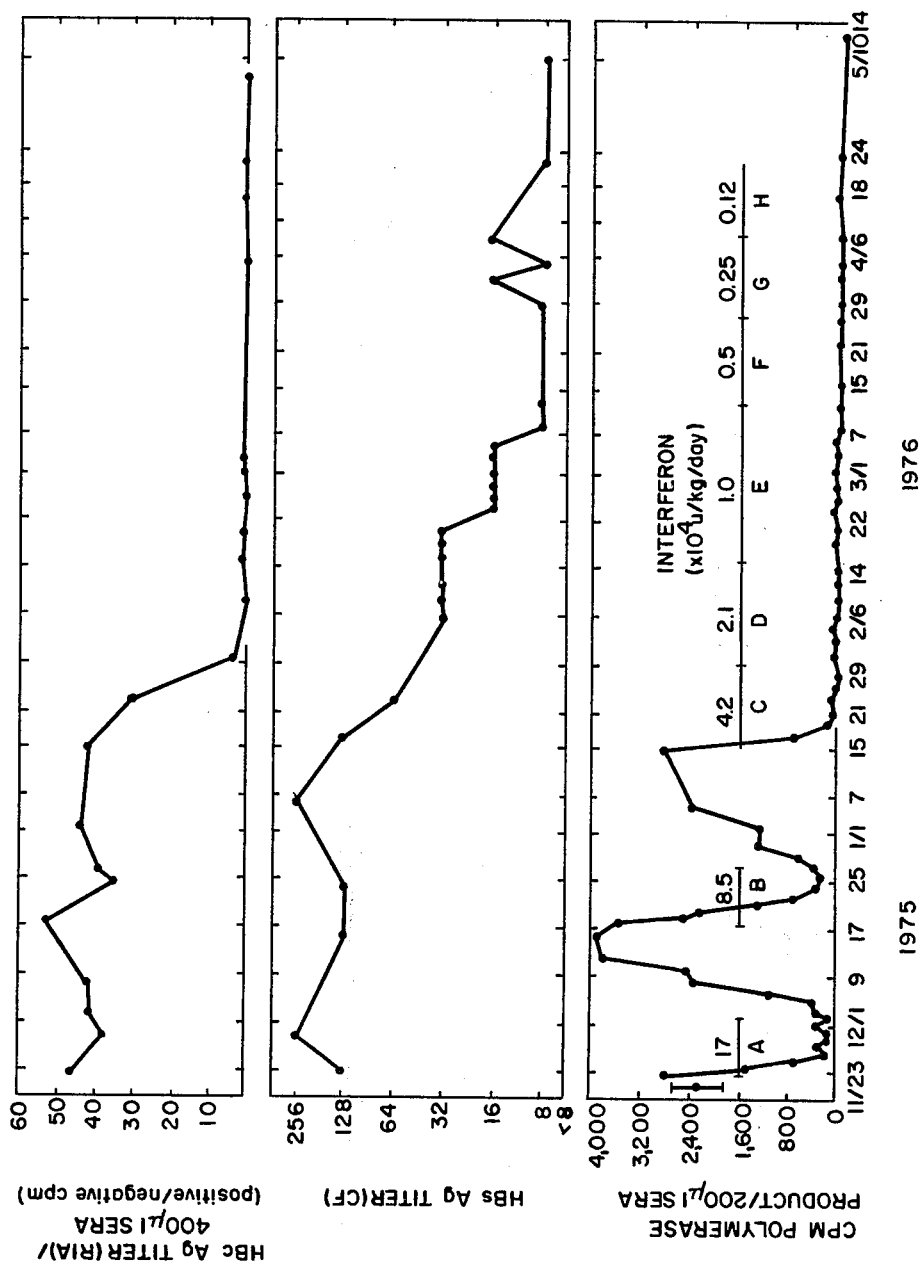
FIG. 2 illustrates the effect of three separate courses (A, B, and C-H) of human leukocyte interferon on Dane particle-associated DNA polymerase, $HB_sAg$ and $HB_cAg$ in patient 1.
Figure 3:
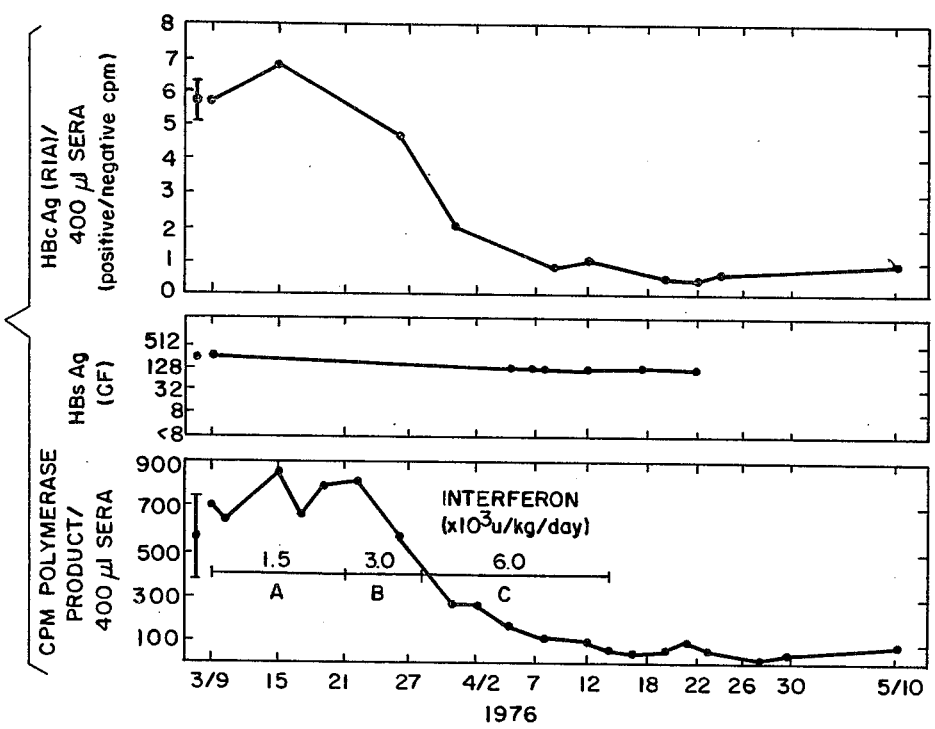
FIG. 3 illustrates the effect of two separate courses (A and B) of human leukocyte interferon on Dane particle-associated DNA polymerase, $HB_sAg$ and $HB_cAg$ in patient 2.
Figure 4:
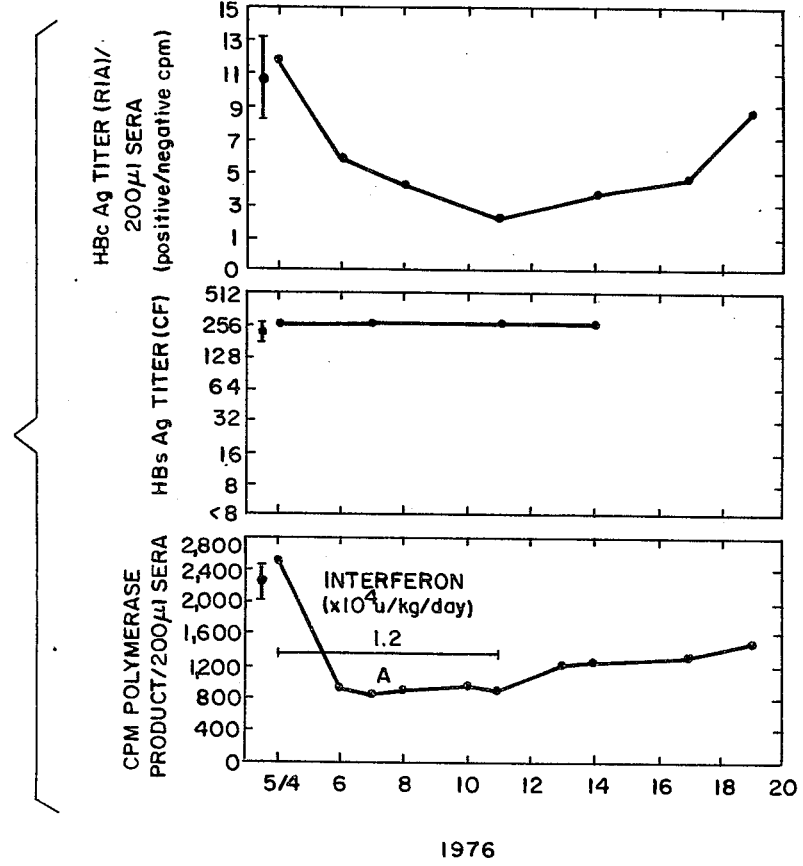
FIG. 4 illustrates the effect of one course (A) of human leukocyte interferon on Dane particle-associated DNA polymerase, $HB_sAg$ and $HB_cAg$ in patient 3.

Parenteral interferon given in a dosage range between $17 \times 10^4$ U/kg/day and $6.0 \times 10^3$ U/kg/day was associated with an immediate and reproducible fall in DNA polymerase levels. In Patient 1 (FIG. 2), three successive courses of interferon were all associated with a 10-fold or greater decrease in polymerase levels. In Patient 2 (FIG. 3), interferon dosage was gradually increased until at a dose level of $6.0 \times 10^3$ U/kg/day, a significant fall in the polymerase level occurred. In Patient 3 (FIG. 4), an intermediate dose of $1.2 \times 10^4$ U/kg/day also led to a prompt fall in polymerase activity. Comparison of the reduction in polymerase level produced in Patient 3 to that observed in Patient 1 (courses A and B) suggests that the higher dosages produced a more complete effect. Patient 4 (no figure), who had no detectable polymerase prior to interferon therapy, remained polymerase negative throughout a one-month treatment with the drug being given at a dosage of $7.5 \times 10^3$ U/kg/day. Human leukocyte interferon was added to polymerase-containing sera in vitro at concentrations of 2000 and 100 units/ml. No effect on polymerase activity was observed when such a mixture was incubated at 37° C. for 2 hours and room temperature overnight.

Interferon, when given for 10 days or less at a dosage range between $17 \times 10^4$ U/kg/day (Patient 1, FIG. 2), and $1.2 \times 10^4$ U/kg/day (Patient 3, FIG. 4), was associated with only a transient fall in polymerase. When therapy was stopped, polymerase values promptly rose toward pretreatment levels. More prolonged therapy (FIGS. 2 and 3) at dosages of $6.0 \times 10^3$ U/kg/day or greater suppressed polymerase activity in a more permanent fashion and subsequent studies have shown that this suppression to depressed or negative polymerase values has lasted for at least several weeks following the termination of therapy.

Other Dane particle markers including $HB_cAg$ and Dane particle-associated DNA were similarly affected. In Patient 1 (FIG. 2) $HB_cAg$ fell only slightly and transiently during courses A and B but became undetectable during more prolonged treatment (courses C and H). In Patient 2 (FIG. 3), a concurrent fall of $HB_cAg$ and polymerase was observed. Again in these two subjects following prolonged interferon therapy, $HB_cAg$ remained down. Patient 3 (FIG. 4), who was treated for 8 days, showed only a transient fall in $HB_cAg$. Patient 4 had no detectable $HB_cAg$ throughout the study. Interferon affected Dane particle-associated DNA in the same fashion as DNA polymerase activity (Patients 1, 2, and 3, Table 3.

The effect of interferon therapy on $HB_sAg$, a viral protein not exclusively associated with Dane particles, appeared to be more variable. In no case did it appear that short-term interferon (Patients 1 and 3, FIGS. 2 and 4), had a measurable effect on $HB_sAg$ levels. Of the three patients treated for a month or longer (Patients 1, 2, and 3, FIGS. 2 and 3), only Patient 1 had a significant change in $HB_sAg$ level. In this patient who received the highest doses of interferon, $HB_sAg$ fell 16-fold from CF titer of 1/128 to 1/8. Patient 2 (FIG. 3) showed no change in $HB_sAg$ and Patient 4 (not shown) had a constant titer of 1/32 throughout the study.

In the case of Patient 1, treatment was started during November 1975 and this treatment was terminated in February 1977. Since the patient's removal from daily interferon through March 1977, the serum aspartate aminotransaminase has been normal and post-treatment liver biopsy is noted as histologically normal by the pathologist.

TABLE 3

Effect of Interferon on Hepatic and Hematologic Function with Serum Interferon Levels

|  | Serum Aspartate Aminotransaminase* | White Blood Cell Count | Peak Serum Interferon Level |
|---|---|---|---|
| Patient 1 | | | |
| Prior to Interferon | 47 – 70 (50)** | 8,100 – 9,400 (8,500)*** | <10 |
| COURSE A | 41 – 69 (51) | 3,400 – 4,000 (3,900) | 1,250 |
| B | 41 – 47 (43) | 3,600 – 4,800 (4,400) | — |
| C | 130 – 294 (218) | 5,000 – 5,500 (5,200) | 210 |
| D | 119 – 165 (139) | 4,900 – 5,600 (5,200) | 89 |
| E | 75 – 159 (102) | 5,300 – 7,700 (6,400) | 50 |
| F | 52 – 74 (63) | 6,000 – 7,100 (6,600) | 23 |
| G | 35 – 52 (44) | 7,200 – 8,100 (7,600) | 16 |
| H | 31 – 35 (33) | 8,100 | — |
| Patient 2 | | | |
| Prior to Interferon | 293 – 1790 (896)** | 10,300 – 14,300 (12,700)*** | <10 |
| COURSE A | 117 – 239 (218) | 10,300 – 13,300 (11,800) | 10 |
| B | 251 | 9,800 | 23 |
| C | 463 – 576 (50) | 8,600 – 10,400 (9,200) | 50 |
| Patient 3 | | | |
| Prior to Interferon | 51 – 59 (55) | 4,300 – 5,800 (5,100) | <10 |
| COURSE A | 87 – 93 (90) | 3,200 – 3,700 (3,500) | 47 |
| Patient 4 | | | |
| Prior to Interferon | 25 – 43 (44)** | 4,900 – 7,200 (6,100)*** | <10 |
| COURSE A | 33 – 46 (4) | 4,100 – 5,100 (4,800) | 45 |

*Normal value <15
**Range and ( ) mean of 4 or more determinations over previous 2 months
***Range and ( ) mean of 2 or more determinations over previous 1-2 months

We claim:

1. A method of treating chronic viral hepatitis B in a human host to effectively and positively reduce markers of infectivity which comprises treating said host parenterally with an effective therapeutic dosage per diem of exogenous interferon for an extended period of time greater than 21 days in the range of $17 \times 10^4$ - $6.0 \times 10^3$ U/kg.

2. The method according to claim 1 wherein the duration of treatment is greater than 21 days and up to 14 months.

3. The method according to claim 1 wherein the reduction of DNA polymerase as a marker of infectivity persists substantially after cessation of treatment.

4. The method according to claim 1 wherein the marker of infectivity for chronic hepatitis B is reduced to a level where the human host is no longer considered an infectivity risk and remains at this level for a sustained period of time.

5. The method according to claim 1 wherein the effective therapeutic dosage per diem of interferon induced in the host by PICLC introduced parenterally to produce a therapeutic blood level of interferon in the host is at least 50 U per milliliter or higher for an extended period of time and results in a decrease of markers of infectivity.

* * * * *